US008768427B2

(12) United States Patent
Sjaaheim et al.

(10) Patent No.: US 8,768,427 B2
(45) Date of Patent: Jul. 1, 2014

(54) ELECTRODE FIXING DEVICE

(76) Inventors: Haldor Sjaaheim, Oslo (NO); Odrun Flatabo, Oslo (NO)

( * ) Notice: Subject to any disclaimer, the term of this patent is extended or adjusted under 35 U.S.C. 154(b) by 118 days.

(21) Appl. No.: 13/319,319

(22) PCT Filed: May 6, 2010

(86) PCT No.: PCT/NO2010/000172
§ 371 (c)(1),
(2), (4) Date: Nov. 7, 2011

(87) PCT Pub. No.: WO2010/128867
PCT Pub. Date: Nov. 11, 2010

(65) Prior Publication Data
US 2012/0053442 A1 Mar. 1, 2012

(30) Foreign Application Priority Data

May 7, 2009 (NO) .................................. 20091811

(51) Int. Cl.
*A61B 5/0478* (2006.01)
*A61B 5/00* (2006.01)

(52) U.S. Cl.
CPC ............. *A61B 5/0478* (2013.01); *A61B 5/6803* (2013.01); *A61B 5/6814* (2013.01); *A61B 2562/046* (2013.01); *A61B 2562/168* (2013.01)
USPC .......................................... 600/383; 600/393

(58) Field of Classification Search
CPC .. A61B 5/0478; A61B 5/6803; A61B 5/6814; A61B 2562/046; A61B 2562/168
USPC ................... 600/383, 393, 544, 545; 607/139
See application file for complete search history.

(56) References Cited

U.S. PATENT DOCUMENTS

| 5,357,957 | A  | * | 10/1994 | Itil et al. ........................ 600/383 |
| 7,715,894 | B2 | * | 5/2010  | Dunseath et al. ............. 600/383 |
| 7,896,823 | B2 | * | 3/2011  | Mangrum et al. ................ 601/9 |

FOREIGN PATENT DOCUMENTS

| JP | 2006-6667 A | | 1/2006 |
| SU | 676273 | * | 7/1979 |
| SU | 676273 A | | 7/1979 |

OTHER PUBLICATIONS

Norwegian Search Report, Date of Report Dec. 1, 2009, 2 pages, Patent No. 20091811.
International Search Report, Date Completed Aug. 20, 2010; 3 pages, PCT/NO2010/000172, European Patent Office.

* cited by examiner

*Primary Examiner* — Lee S Cohen
(74) *Attorney, Agent, or Firm* — Haynes and Boone, LLP

(57) ABSTRACT

The present invention concerns a device and a method for placing and securing sensors/electrodes on the head of an individual. The device/method optimizes signal information and avoids some of the problems connected to the devices and methods in the prior art. The device comprises a rigid, fluid-proof outer layer, an elastic, fluid-proof inner layer with placement points for sensors or electrodes, and a middle layer comprising a fluid between inner and outer layers. The invention also comprises a device for regulating the pressure of the fluid. Inner and outer layers are joined together to form a cavity for receipt of the middle layer.

17 Claims, 4 Drawing Sheets

ELECTRODE FIXING DEVICE

Figure 1:
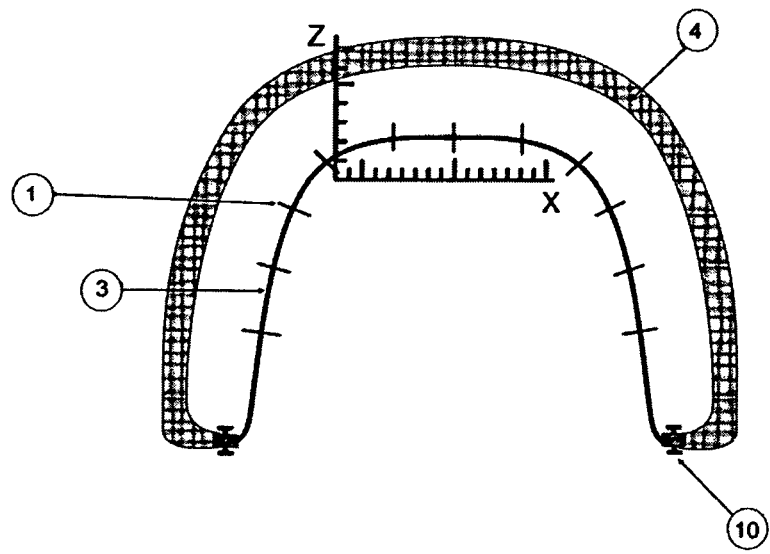

The present application is a U.S. national-stage patent application of international patent application PCT/NO2010/000172, filed May 6, 2010, which claims priority to Norwegian Patent Application No. 20091811, filed May 7, 2009, the disclosures of each of which is incorporated herein by reference in its entirety.

TECHNICAL FIELD OF THE INVENTION

The invention concerns a device and a method for placing and securing sensors/electrodes on the head of an individual.

BACKGROUND OF THE INVENTION

Measurements of the electrical activity of the brain are, due to historical reasons, especially widespread in Europe and Russia within neurophysiologic and psychophysiologic diagnostics. Since 1960 the development regarding biofeedback treatment has for a large part been performed in the USA, Canada, Australia, Europe and Russia. As known within the field there exists both biological and technical methods for measuring and influencing different types of activities in the brain. The most common methods are: Electroencephalography (EEG), Hemoencephalography (HHG) and Magnetoencephalography (MEG). Within QEEG (quantitative EEG measurements) several mathematical models have been developed in order to measure discriminant functions that comprise: power-coherence, phase, IFTA pre vs. post treatment statistics, low RATE, instant coherence phase & Z-score biofeedback and others. QEEG is performed as a common EEG-recording, where an operator arranges several (21+) electrodes on the head of an individual in order to register a large part of the electrical activity of the brain at the same time. The brain activity is registered during a time period and functional assignements beyond the standard, eyes open and shut, may be added. The information is often compared to the activity which is analyzed by all of the various software systems that the operator has installed. The different types of software utilises different mathematical models for diagnosis, while others use systemic models, also called protocols, for treatment. Amongst other things, it is important that the electrodes in the QEEG system are placed in a correct manner, and that the contact between the electrodes and scalp is good. This is important in order to obtain an optimal basis for comparison between two measurements, or for comparing measurements from two or several individuals. Therefore, as a standard, the electrodes are placed in accordance with the international 10-20 system (described by for instance Erns Niedermeyer, Fernando Lopes da Silva, Electroencephalography: Basic Principles, Clinical Applications, and Related Fields, page 140). It is challenging to obtain the same result from two measurements. A more standardized system, than the sum of what exists today, would be very advantageous with regard to the further development of the science and research within this field.

Most EEG and QEEG systems today are based on elastic mesh and/or caps which are adapted to the 10-20 system, or other less known placement-charts. These caps are made in various designs with apertures for inserting electrodes. The caps are also made in several different sizes since the distance between the electrodes must be adapted to the size of the skull in accordance to the 10-20 system, or other placement-charts. The problem is often that these caps are not capable of furnishing the electrodes with enough pressure against the skull, due to hair and the shape of the skull. Caps that are tightened are often uncomfortable for the individual, and especially for sensitive children. Optimization is necessary to achieve a signal without too much background noise. Such noise will lead to less accurate measurements and information. The electrodes must also be placed manually in a correct manner with regard to the different sizes of the skull, and this is often time consuming and requires competence. Further, such manual placing of the electrodes increases the risk of placing the electrodes in an erroneously manner due to human failure.

Patent application US 2007/0106170 A1 discloses an electrode/sensor cap for use in EEG. Multiple inflatable bladders are used to achieve pressure on the electrodes. The technical solution of using inflatable bladders according to said application requires multiple caps adapted to individual skull sizes, and manual adaptation of the electrode placing is still necessary.

The Russian patent application SU 676273 A1 discloses an electrode/sensor cap for use in EEG. The technical solution for achieving adequate pressure on the electrodes is similar to the one disclosed in US patent application no. 2007/0106170 A1. The multiple bladders are here formed by joining the inner layer of the cap to the outer shell/layer in such a way that a discrete bladder is formed at each electrode. The drawbacks of said solution are the same as those mentioned for the US patent application no. 2007/0106170 A1.

Japanese patent application JP 2006-6667 A discloses an electrode/sensor cap for use in EEG. In one of the embodiments, a separate balloon situated between an inner hat and an outer helmet is inflated to provide pressure on the electrodes placed on the inner hat. The same drawbacks apply for the electrode/sensor cap of JP 2006-6667 A as the ones mentioned for patent application US 2007/0106170 A1

Measurements of the electrical activity of the brain are also used in a number of other areas in addition to neurophysiologic/psychophysiologic diagnostics and treatment. In the area of biotechnology it is possible, by using such measurements, to transform electrical impulses from the brain to electronic signals by the help of suitable sensors; such signals may in turn guide/control various technical systems. These technical systems may be for example fighter pilot helmets, speech synthesizers, robots, various entertainment systems such as computer games as well as other systems making use of brain-computer interfacing (BCI).

It is the purpose of the present invention to provide a device, and a method, for placing and securing sensors/electrodes on the head of an individual. Said device/method optimizes signal information and avoids some of the problems connected to the devices and methods in the prior art.

SUMMARY OF THE INVENTION

The present invention concerns a device, and a method, for placing and securing sensors/electrodes on the head of an individual. Said device/method optimizes signal information and avoids some of the problems connected to the devices and methods in the prior art.

The device, its use and method according to the invention are defined by the appended claims.

Said device may replace the presently used prior art caps. The device has an inner cap/layer that is constructed in a fluid-proof elastic material having a fluid-proof directly joined to an outer rigid shell/layer. The direct joining is along the circumference of the inner cap/layer enabling the homogenous expansion of said inner cap/layer. The middle layer, between the outer shell and the inner cap, comprises a fluid and/or a material that may be compressed/expanded in a uniform manner depending on the gas pressure or amount of fluid. The elastic cap/layer is slightly smaller in size than the smallest head to which it shall fit. This is due to the fact that the inner layer must be able to apply pressure to the EEG electrodes against the skull to achieve an optimal signal. A gas or fluid pump provides an underpressure/vacuum to develop between the rigid outer shell and the inner elastic cap by withdrawing fluid from the middle layer. The elastic cap will then expand homogenously to a size larger than the individuals head. Then the individual puts the helmet on and fluid is released back into the middle layer by use of a means for regulating pressure, for instance a valve, so that the inner layer shrinks and provides pressure on the electrodes, pushing them against the skull. The fact that the elastic cap is expanded homogenously also causes the distances between the electrodes to increase homogenously. This device/helmet causes the distance between the electrodes to be regulated properly independent of the individuals head size, when using for example the 10-20 system. Time and use of resources may be utilized better and a more standardized system for QEEG analyzes is achieved. In addition, neither time consuming individual adaptation, nor a large number of caps of different sizes adapted to each individual, will be necessary.

The present invention is primarily developed for use together with EEG sensors, but is not limited to this use, and may without any other requirements be adapted for use with sensors like MEG and HEG, as well as other sensors developed for use in measurements of the brains activity.

SHORT DESCRIPTION OF THE DRAWINGS

FIG. 1: Cross section of a device according to the invention seen from the front, without vacuum.

Figure 2:
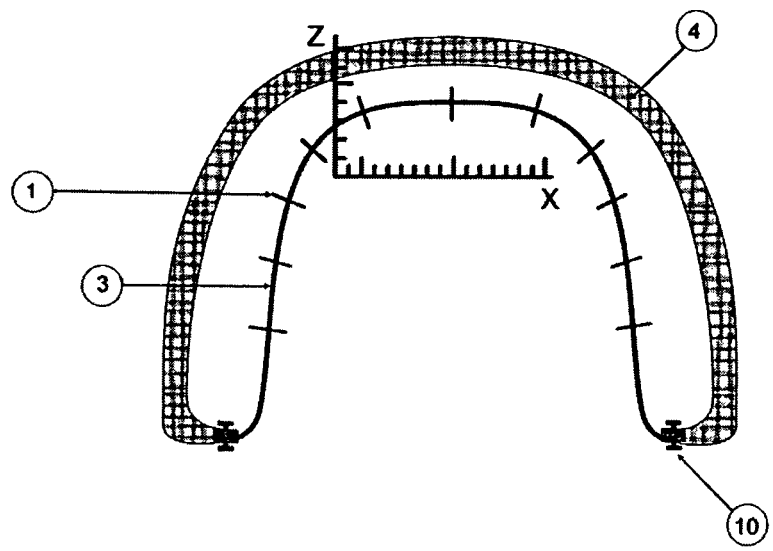

FIG. 2: Cross section of a device according to the invention seen from the front, with vacuum.

Figure 3:
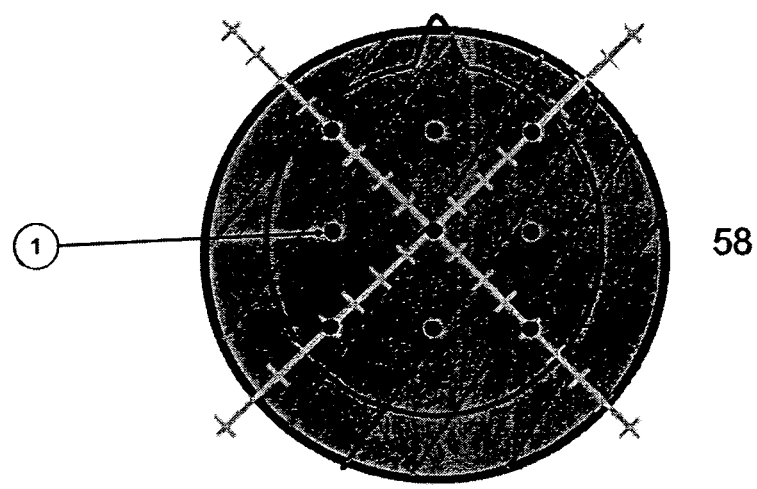

FIG. 3: An example of the arrangement of the electrodes on the inner cap when the individual have a large sized head.

Figure 4:
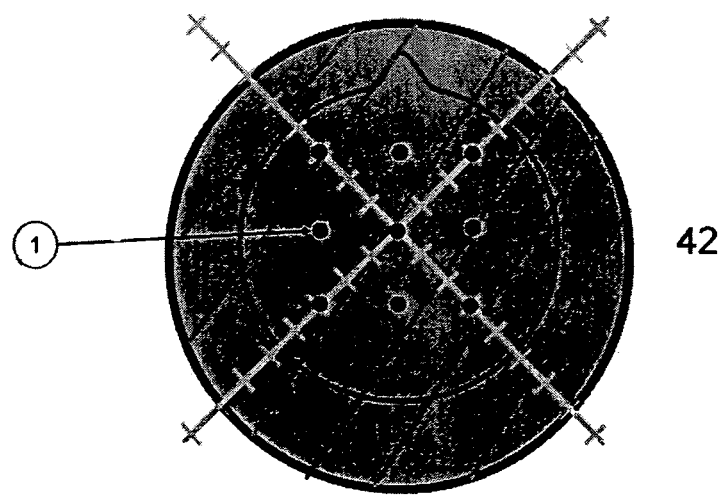

FIG. 4: An example of the arrangement of the electrodes on the inner cap when the individual have a small sized head.

Figure 5:
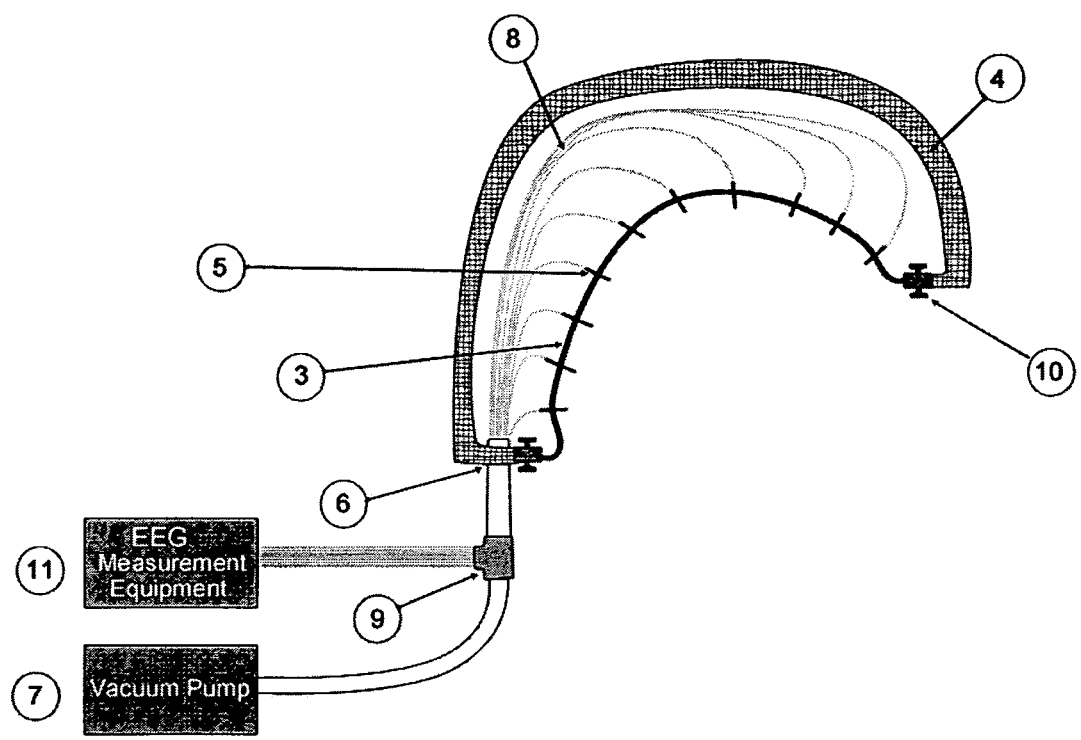

FIG. 5: Cross section of a device according to the invention seen from the side without vacuum.

Figure 6:
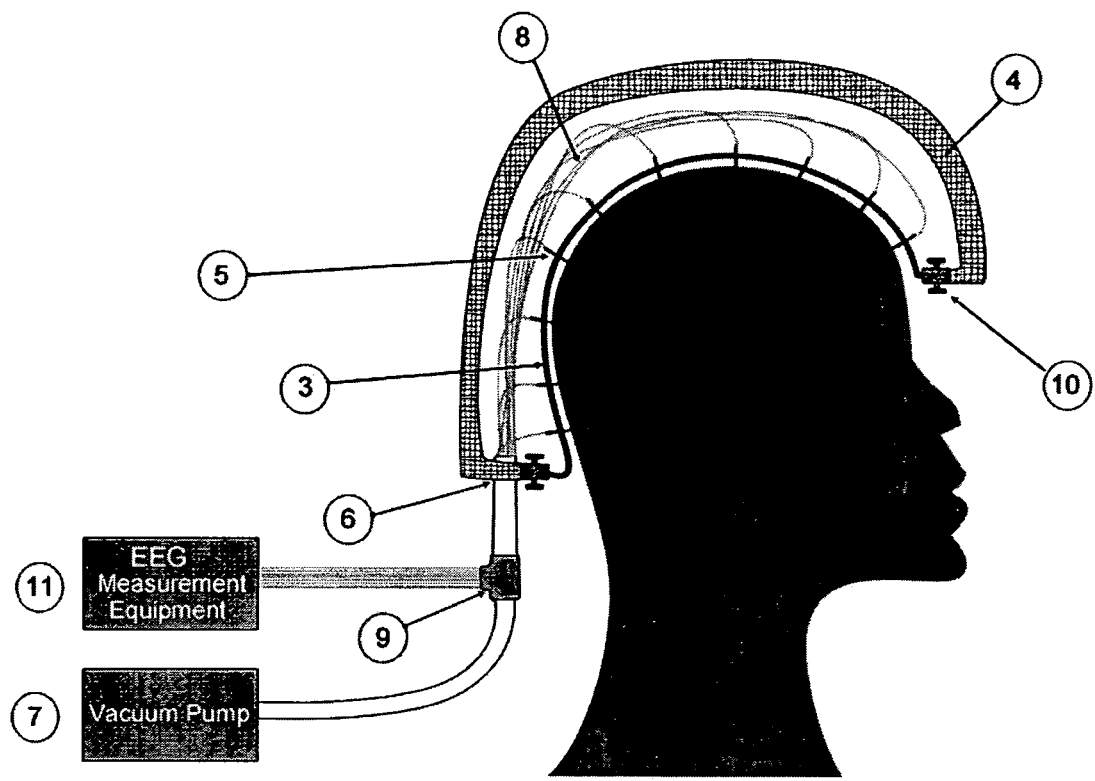

FIG. 6: Cross section of a device according to the invention seen from the side with vacuum, after adaptation to an individual.

DETAILED DESCRIPTION OF THE INVENTION

The present invention have many areas of use, like EEG, HEG and MEG, but it is in the following described more detailed with regards to its use in QEEG (Quantitative Electroencephalography) in order to illustrate which problems the invention solves. QEEG is a type of EEG where an operator places several (21+) electrodes on an individual's head in order to register the brains electrical activity. The brain activity is registered over a period of time, and is often presented as a topographical map. The topographical maps are often compared to normative databases (databases containing topographical maps). Therefore, it is important that the electrodes in the QEEG system are placed correctly in order to achieve a proper basis for comparison. Usually, the electrodes are therefore arranged in accordance to the international 10-20 system. It is challenging to achieve the same results in two separate measurements, and a system, more standardized than what exists today, would therefore be advantageous. Other placement charts than the 10-20 system may also be used.

FIG. 1 shows the distance between the electrodes/sensors 1 before the fluid is pumped out of the middle layer 2. When the fluid is pumped out, FIG. 2, the elastic inner cap 3 will expand uniformly, and the distances between the electrodes/sensors along the X-axis will increase correspondingly. FIGS. 3 and 4 show the distances between the electrodes/sensors along the X- and Y-axis, when an individual using the helmet has a large size head (for instance an adult, here with a head size 58, FIG. 3) and when an individual has a small size head (for instance a child, here with a head size 42, FIG. 4), respectively. In this manner the electrodes will attain a correct placing independent of the head size of the individual using the device/helmet.

FIGS. 5 and 6 shows one specific embodiment of the invention. Here shown as a type of helmet comprising a rigid outer shell 4 and an elastic inner cap 3, joined together by a fluid-proof joint 10. The joint 10 is preferably constructed in such a way that the elastic cap may be taken on and off in order to facilitate cleaning and repair of electrodes/sensors 5, switch type of cap 3 and so forth. The electrodes/sensors 5 are fasten on, and penetrates, the elastic cap 3 by use of a fluid-proof joint and the wires 8 belonging to said electrodes/sensors are led out through a fluid-proof joint 6. The wires 8 are connected to EEG measuring equipment 11. The fluid pressure is regulated by a vacuum pump 7 connected through the outer rigid shell 4 using a valve 9. In this embodiment, the fluid used in the middle layer is air. In order for the elastic inner cap 3 to expand homogenously and unhindered it is only directly joined to the rigid outer shell 4 along the circumference of the inner cap 3, by way of the joint 10.

The material used in the cap 3 may be any suitable elastic material that is fluid-proof. These include different types of natural or synthetic rubbers and elastomers. More specific, the material may be for example latex or neoprene. The cap may have a variable number of points for attaching sensors/electrodes 5. The number of electrodes/sensors, and the arrangement of these, will depend on the type of method for measuring that is used.

The material in the outer shell 4 may be any suitable rigid material, including different types of plastic, glass fiber, metal, fiber reinforced plastic, ceramic materials etc.

The material used in the layer 2 between the outer shell 4 and the inner cap 3 is a fluid, like air, water or oil, optionally in combination with any suitable material that may be uniformly compressed/expanded depending on fluid pressure, like for instance a foam, polymer, foam rubber or sponge.

The number of electrodes/sensors may be varied from 1 to 256 depending on which method is used. In the FIGS. 1-2 and 5-6, the number of electrodes visible on the cross sections is in accordance with a cap containing 128 electrodes.

In EEG-measurements, in addition to the above-mentioned electrodes, two reference or earthing electrodes that are not dependent on being integrated into the helmet, but are fastened to the ears by a type of copper clamp and gel, are used. These may also be integrated into the helmet. The reference electrodes are essential and are used in all QEEG setups, but since they are fastened to the ear lobe or the mastoid (right behind the ear) it is not necessary to use the present system in order to optimize the position.

The electrodes/sensors can be of any type that is used for measurements of signals in the brain. When used in medical/neuropsychological diagnostics and treatment, "wet" electrodes are preferred since these provide the best signal. With the term "wet" electrodes are meant electrodes which are used in combination with a gel/paste/liquid to provide better contact with the scalp. In other applications, where the demands for signal quality are not as high, dry electrodes may also be used, and in many cases be preferred since these are cheaper and more easy to use.

In the shown embodiment, the wires 8 from the electrodes are led out through the outer shell. In other embodiments said wires may be bundled and connected to a transmitter/receiver incorporated on or inside the helmet/outer shell, and the signals may thereby be transmitted wireless to an external receiver.

The present invention will contribute to increase the reproducibility of EEG-measurements, make it possible to perform such and other measurements (HEG and MEG) faster due to the simplified adaptation of the electrodes/sensors and avoid the need of having sensor/electrode caps in different sizes. In addition, the invention makes it easier to integrate for instance EEG-measurements for use in activities such as controlling/steering of airplanes, robots, computer programs and games, as well as other uses of BCI (brain computer interface).

The joining 10 can be achieved by any suitable fluid-proof means such as, for instance gluing, welding, clamps, a zipper or a clamp or clip list.

The helmet may also be equipped with a chin strap to further stabilize the position/placement on the head. Other solutions providing such an effect may be the use of bows, ear muffs or something similar.

The invention claimed is:

1. A device for positioning and fixing of sensors on the scalp of an individual, the device comprising:
   a rigid, fluid-proof outer layer;
   an inner layer comprising an elastic, fluid-proof material having a plurality of points for the placement of sensors or electrodes, said inner layer defining a circumference;
   a middle layer disposed between the outer layer and the inner layer, the middle layer comprising a fluid having a fluid pressure; and
   a vacuum pump and a valve fluidly coupled to said middle layer for regulating the fluid pressure of the middle layer;
   wherein the inner layer is joined to the outer layer only at the circumference of the inner layer.

2. The device of claim 1, further comprising a plurality of electrodes or sensors attached to the inner layer at the points.

3. The device of claim 2, wherein the electrodes are selected from the group consisting of EEG, MEG and HEG electrodes.

4. The device of claim 1 wherein the fluid pressure is less than an ambient pressure.

5. The device of claim 1, wherein the inner layer is made of a natural or synthetic rubber.

6. The device of claim 1, wherein the middle layer further comprises sponge or foam rubber.

7. The device of claim 1, wherein the fluid is air.

8. The device of claim 1 further comprising:
   a plurality of sensors attached to the inner layer at the points, wherein the sensors are selected from the group consisting of EEG, MEG and HEG sensors;
   wherein the inner layer comprises rubber selected from the group consisting of latex and neoprene; and
   wherein the fluid is air.

9. A method for placement of electrodes/sensors on the scalp of an individual, the method comprising the steps of:
   withdrawing fluid from between an outer layer and an inner layer of a device for placing electrodes on the scalp of an individual so that the pressure between the outer and inner layers is below the ambient pressure;
   placing said device on the head of an individual; and
   releasing fluid between the outer and inner layers to cause the inner layer to exert pressure on electrodes/sensors adjacent the scalp.

10. The method of claim 9, further comprising the step of attaching a plurality of electrodes to the inner layer.

11. The method of claim 9, further comprising the step of adjusting the relative spacing between electrodes by regulating the fluid pressure.

12. The method of claim 9, further comprising the step of measuring electrical activity of the brain of a an individual.

13. The method of claim 9, wherein the electrodes/sensors are placed in accordance with the 10-20 system.

14. The method of claim 9, further comprising the step of providing a device having
   a rigid, fluid-proof outer layer;
   an inner layer comprising an elastic, fluid-proof material having a plurality of points for the placement of electrodes/sensors;
   a middle layer disposed between the outer layer and the inner layer, the middle layer comprising a fluid having a fluid pressure;
   a plurality of electrodes/sensors attached to the inner layer at the points;
   a vacuum pump and a valve;
   wherein the inner layer comprises rubber selected from the group consisting of latex and neoprene; and
   wherein the fluid is air.

15. A sensor placement system positioning sensors adjacent the scalp of an individual, the system comprising:
   a helmet comprising:
      a rigid, fluid-proof outer layer;
      an inner layer defining a circumference and comprising an elastic, fluid-proof material, wherein the inner layer is joined to the outer layer only at the circumference to form a single fluid tight cavity therebetween; and
      a fluid disposed in the fluid tight cavity, the fluid having a fluid pressure;
   a plurality of sensors attached to the inner layer of the helmet;
   a vacuum pump in fluid communication with the fluid tight cavity and disposed to pump fluid out of the cavity.

16. The system of claim 15, wherein the helmet further comprises a chin strap attached to the outer layer.

17. The system of claim 15, further comprising a wireless transmitter electrically attached to the sensors.

* * * * *